(12) United States Patent
Nelson et al.

(10) Patent No.: US 8,324,191 B2
(45) Date of Patent: Dec. 4, 2012

(54) COMBINED CALCIUM, MAGNESIUM AND VITAMIN D SUPPLEMENTS

(75) Inventors: Deanna Jean Nelson, Raleigh, NC (US); Walter C. Holberg, III, Apex, NC (US)

(73) Assignee: Biolink Life Sciences, Inc, Cary, NC (US)

( * ) Notice: Subject to any disclaimer, the term of this patent is extended or adjusted under 35 U.S.C. 154(b) by 424 days.

(21) Appl. No.: 12/218,067

(22) Filed: Jul. 11, 2008

(65) Prior Publication Data

US 2010/0009948 A1    Jan. 14, 2010

(51) Int. Cl.
    *A01N 37/36*    (2006.01)
    *A01N 45/00*    (2006.01)
(52) U.S. Cl. ....................................................... 514/167
(58) Field of Classification Search .................... 514/167
See application file for complete search history.

(56) References Cited

U.S. PATENT DOCUMENTS

| | | | |
|---|---|---|---|
| 6,288,106 B1 * | 9/2001 | Pearson et al. | 514/440 |
| 6,451,341 B1 | 9/2002 | Slaga et al. | |
| 7,060,295 B2 * | 6/2006 | Richardson et al. | 424/464 |
| 2001/0031744 A1 | 10/2001 | Kosbab | |

FOREIGN PATENT DOCUMENTS

| | | |
|---|---|---|
| EP | 0514451 | 1/1997 |
| WO | 9639203 | 12/1996 |

OTHER PUBLICATIONS

Montero-Odasso et al. (Molecular aspects of Medicine, 26, (2005), 203-219).*
Golden, Nevllie H. (Adolescent Medicine, vol. 14, No. 1, pp. 97-108Feb. 2003).*
Shvde et al. (PNAS, Oct. 15, 2002), vol. 99, No. 21, pp. 1387-13491.*
Golden, Nevile H. (Int. J. Adolesc. Med. Health (2002):14(1):9-17.*

* cited by examiner

*Primary Examiner* — San-Ming Hui
(74) *Attorney, Agent, or Firm* — Casimir Jones SC

(57) ABSTRACT

The present invention relates to oral nutritional and therapeutic products which are useful for providing vitamins and minerals required for bone health. The present invention is an oral nutritional and therapeutic composition of calcium succinate, magnesium R-(+)-alpha-lipoate, and Vitamin D for use in the maintenance of bone health, the optimization of bone growth, reducing the risk of bone fracture, and the prevention and treatment of osteoporosis. The pharmaceutical products and methods of the present invention are particularly useful in building bone mass, quality, and density during growth, maintaining bone mass, quality, and density over time, reducing bone fracture risk, and treating osteoporosis in men and women.

6 Claims, No Drawings

COMBINED CALCIUM, MAGNESIUM AND VITAMIN D SUPPLEMENTS

FIELD OF THE INVENTION

The present invention relates to oral nutritional and therapeutic products which are useful for providing vitamins and minerals required for bone health. The present invention is an oral nutritional and therapeutic composition of calcium succinate, magnesium R-(+)-alpha-lipoate, and Vitamin D for use in the maintenance of bone health, the optimization of bone growth, reducing the risk of bone fracture, and the prevention and treatment of osteoporosis. The pharmaceutical products and methods of the present invention are particularly useful in building bone mass, quality, and density during growth, maintaining bone mass, quality, and density over time, reducing bone fracture risk, and treating osteoporosis in men and women.

BACKGROUND OF THE INVENTION

Calcium. Calcium, a physiologically essential mineral, plays a central role in building stronger, denser bones early in life and in maintaining strong and healthy bones later in life. In addition, calcium functions in cardiac regulation, blood clotting, nerve signal conduction, stimulating hormone secretion, muscle contraction, and other diverse physiological processes.

In the absence of calcitriol, intestinal absorption of calcium is solely by the passive, extracellular route, which limits gross absorption from the gastrointestinal tract to about 10% of dietary intake. Absorption results in transient serum hypercalcemia, and about half of the calcium absorbed from the gastrointestinal tract spills into the urine and is excreted. Concurrently, the body loses calcium through skin, nails, hair, sweat, and excretion. Dermal losses of calcium in sweat are unregulated. Under sedentary conditions, cutaneous losses alone are estimated to be on the order of 0.4 to 1.4 mmol calcium per day, but with exercise and sweating, such losses can rise to above 7 mmol calcium per day. This drain is great enough to produce a measurable change in bone mass across an athletic playing season, for example. The lost calcium must be replaced, or the body will take calcium from the bones to perform other functions.

It is well known that augmented calcium intakes build and maintain peak bone mass, structure and quality during growth and repair; slow age-related bone loss; prevent fractures resulting from osteoporosis; and reduce fragility fractures in the elderly. Moreover, there is general agreement that a high peak bone mass is strong protection against low bone mass and its associated fragility later in life.

Vitamin D. Vitamin D, not a normal constituent of most foods, is typically produced endogenously by a cutaneous photosynthetic reaction. Solar ultraviolet radiation converts endogenous 7-dehydrocholesterol into pre-vitamin $D_3$, which then rapidly isomerizes in the skin to cholecalciferol (vitamin $D_3$). Cholecalciferol is stored bound to D-binding protein. Upon release from storage, cholecalciferol is converted to 25-hydroxy vitamin $D_3$ [$25(OH)D_3$; ergocalciferol] in the liver and kidneys. Subsequently, $25(OH)D_3$ is hydroxylated in the kidney to $1,25(OH)_2D_3$ (calcitriol). Calcitriol functions as a hormone, enhancing calcium absorption by binding to a mucosal nuclear receptor and inducing the synthesis of calcium-binding transport protein needed for active calcium absorption across the intestinal mucosa. In addition, $25(OH)D_3$ plays a role in calcium and magnesium transport by binding to mucosal receptors and augmenting active transport in cells in which calcium- and magnesium-binding proteins have been expressed.

Vitamin D plays an essential role in calcium and magnesium homeostasis. In addition, vitamin D is essential for optimal physiological functioning of a spectrum of other cells and tissues, including the brain. Other functions of vitamin D include regulation of proliferative and apoptotic activity, immunomodulatory and prodifferentiation activity, and interaction with the rennin-angiotensin system, insulin secretion, and neuroprotective activity.

Vitamin D status is currently indicated by 25-hydroxycholecalciferol ($25OHD_3$) concentration in serum. The National Academy of Sciences (NAS) used a cutoff value of 27.5 mmol/L (<11 ng/mL) $25OHD_3$ to indicate "vitamin D deficiency" for the purposes of setting Dietary Reference Intakes for vitamin D.

Magnesium. Magnesium is the fourth most prevalent element in the body and the second most abundant intracellular ion. Since magnesium is a cofactor in over 300 enzyme systems, adequate magnesium is essential for many biosynthetic processes, glycolysis, formation of adenosine-3",5"-cyclic monophosphate, energy-dependent membrane transport, and transmission of the genetic code. Magnesium makes up 0.5-1% of the bone and plays a role in both matrix and mineral metabolism in bone. Magnesium depletion causes cessation of bone growth, decreased osteoblastic and osteoclastic activity, osteopenia, and bone fragility. Patients with significant magnesium deficiency experience tremors, myoclonus, and arrhythmias including ventricular tachycardia, fibrillation, and torsade de pointes.

Adequate serum magnesium levels are needed for proper calcium metabolism. Magnesium deficiency can result in calcium deficiency, peripheral resistance to the effects of vitamin D, and resistance to parathyroid hormone. As a result, adequate calcium intake may not ensure proper bone health if magnesium status is abnormal. Further, under conditions of chronic magnesium insufficiency, although serum magnesium levels are in the low normal range, intracellular magnesium levels may be insufficient to support health.

Bone Health. Bone is not a hard and lifeless structure. It is, in fact, complex, living tissue. Bone breakdown and new bone formation is continuous, and natural changes in bone health reflect the balance between these processes. During youth, bones grow in length and density. During teen years, maximum height is obtained, and almost 40% of adult bone mass is potentially accrued. Bones continue to grow more dense until about age 30 when peak bone density is attained. After that point, bones slowly start to lose density or strength as bones begin to break down faster than new bone can be formed. This imbalance occurs as part of the natural aging process; or as the result of prolonged exposure to certain medications (e.g., steroids, anticonvulsants, certain cancer treatments, and aluminum-containing antacids); chronic disease that affects the kidneys, lungs, stomach, and intestines; or lifestyle habits at any age. Therefore, it is important to optimize bone development and maintenance throughout life by incorporating sufficient calcium, magnesium, and phosphate for bone health in the diet, both as food and as supplements.

Osteoporosis. Osteoporosis is a disease of bone leading to an increased risk of fracture. In osteoporosis, the bone mineral density (BMD) is reduced, bone microarchitecture is disrupted, and the amount and variety of non-collagenous proteins in bone is altered. Osteoporosis is defined by the World Health Organization (WHO) in women as a bone mineral density 2.5 standard deviations below peak bone mass (20-year-old sex-matched healthy person average) as measured by dual energy x-ray absorptiometry. Osteoporosis is most common in women after the menopause, but may develop in men and pre-menopausal women if they suffer from hormonal disorders and other chronic diseases, smoke, or use medications that interfere with calcium absorption.

According to the Surgeon General, osteoporosis and other bone diseases can initiate a downward spiral in physical health and quality of life. Bone disease can also lead to premature death. The 2004 report, *Bone Health and Osteoporosis: A Report of the Surgeon General*, stated that 10 million Americans over the age of 50 have osteoporosis, while another 34 million are at risk for developing the disease. [U.S. Department of Health and Human Services, Public Health Service, Office of the Surgeon General, *Bone Health and Osteoporosis: A Report of the Surgeon General*, 2004] The disease has been implicated as a causative factor in 1.5 million bone fractures each year. In the 2004 report, the Surgeon General warned that by 2020, half of all Americans older than 50 will be at risk for fractures from osteoporosis and low bone mass if no immediate action is taken.

Dose and Form of Conventional Vitamin and Mineral Compositions Supporting Bone Health. Calcium, concurrently supplied with vitamin D, maintains bone health, enables optimal bone growth, and is useful for the prevention and treatment of osteoporosis. As a consequence, calcium with vitamin D is among the most commonly prescribed dietary supplements. The main indication for these prescriptions is the prevention or treatment of osteoporosis and osteoporotic fracture (a bone fracture resulting from severely decreased bone density and debilitating alterations in bone microarchitecture). For example, in a recent randomized, controlled trial of calcium (1 gram calcium/day as the citrate) in 1,471 healthy older women (aged 74+/−4 years), supplemental calcium had a beneficial effect on bone density, reduced fracture incidence, hazard ratios on time to first fracture, and prevention of height loss. [Reid I R, Mason B, Horne A, Ames R, Reid H E, Bava U, Boiland M J, Gamble G D. Randomized controlled trial of calcium in older women. Am J Med 2006; 119(9): 777-785] Likewise, a meta-analysis was carried out of 29 studies in which calcium and/or vitamin D were administered to individuals at age 50 or older. A total of 63,897 subjects were examined in these trials, with a mean age of 67.8 years for all subjects; 92% were women. The analysis showed that both the dose of calcium and the form in which it is provided are significant factors in maintaining bone health. The minimum dose of calcium which appears to be effective is 1200 mg daily. The overall rate of fracture reduction associated with calcium or calcium plus vitamin D supplementation versus placebo was 12% (P=0.0004). The active intervention was associated with a reduced bone loss of 0.54% at the hip and 1.19% at the spine. Greater treatment adherence strengthened the positive outcomes associated with active treatment. Individuals over the age of 70 were particularly likely to benefit from supplementation with calcium alone or calcium plus vitamin D. A second meta-analysis showed that the dose of vitamin D was a significant factor in maintaining bone health, particularly at non-vertebral sites. Researchers analyzed data from 12 randomized, controlled trials and found that vitamin D at a dose of 700 to 800 IU per day reduced the risk of hip fracture by 26% and any non-vertebral fracture by 23%. Both of these results were statistically significant. However, the data showed that vitamin D at a dose of 400 IU per day failed to demonstrate any fracture benefit.

In general, the selection of a calcium supplement is determined by factors such as availability, purity, absorbability, and an individual's tolerance to adverse taste, texture, and side effects of ingestion. Conventionally, several different calcium compounds (Table 1) are used in supplements and therapies for supporting bone health and preventing or treating osteoporosis. The bioavailability of each of these conventional calcium sources is about 10% in the absence of vitamin D. [Heaney R P, Roecker R R, Weaver C M. Absorbability of calcium sources: the limited role of solubility. Calcif Tissue Int 1990; 46: 300-304.]

TABLE 1

Conventional Calcium Sources

| Calcium Source | % Ca, by weight |
|---|---|
| Calcium Acetate | 23% |
| Calcium Carbonate | 40% |
| Calcium Citrate | 21% |
| Calcium Citrate Malate | 24% |
| Calcium Gluconate | 9% |
| Calcium Lactate | 14% |
| "Calcium Phosphate" | 34-40% |

Of the calcium salts listed in Table 1, calcium carbonate contains the highest percentage of calcium by weight (40%) and is the least expensive and most widely used at the present time. However, it is one of the most poorly absorbed and least bioavailable of calcium salts, particularly when administered in high doses. In addition, it is one of the most unpalatable of calcium salts and has a repugnant chalky taste. Further, calcium carbonate often contains trace quantities of toxic metals such as lead, thallium, and aluminum. Alternatively, calcium is conventionally supplied as calcium acetate or calcium citrate. Calcium acetate contains 23% calcium by weight. While it is more palatable than calcium carbonate, ingestion of high doses results in gastric irritation and regurgitation of acetic acid ("vinegar breath"). Calcium citrate contains 21% calcium by weight. This salt is more palatable than calcium carbonate or calcium acetate. However, doses of 1 g calcium citrate daily have been reported to increase risk for myocardial infarction, stroke and death. [Bolland M J, Barber P A, Doughty R N, Mason B, Horne A, Ames R, Gamble G D, Grey A, Reid I R. Vascular events in healthy older women receiving calcium supplementation: randomised controlled trial. Brit Med J 2008 Feb. 2; 336(7638): 262-266.] Calcium phosphate, the other calcium salt with a high percentage calcium is frequently hydroxyapatite ("ground bone") and has a distasteful appearance and chalky taste coupled with poor absorption from the gastrointestinal tract.

Vitamin D insufficiency is common in the United States. The elderly and African-Americans are at particularly high risk of deficiency. Vitamin D deficiency among the elderly causes secondary hyperparathyroidism and osteomalacia and exacerbates osteoporosis, resulting in increased risk of skeletal fractures. The prevalence of vitamin D deficiency or insufficiency, as estimated from the National Health and Nutrition Examination Survey (NHANES) III data for non-institutionalized individuals, indicated that one-half of the elderly women sampled who lived in northern latitudes had vitamin D insufficiency. The incidence among institutionalized and homebound elderly individuals, who spend less time in the sunshine, is potentially much greater.

Magnesium is absorbed in the intestines and then transported to cells and tissues throughout the body. Approximately one-third to one-half of dietary magnesium is absorbed into the body of a healthy individual. Although the percentage absorption of dietary magnesium is high, data from the 1999-2000 National Health and Nutrition Examination Survey suggest that substantial numbers of adults in the United States fail to consume diets containing the recommended amounts of magnesium. In particular, older adults, individuals with digestive or chronic malabsorptive disorders, and individuals with chronically low blood levels of calcium, by way of example, lack sufficient magnesium in the diet.

Conventional magnesium supplements provide magnesium as a salt (Table 2). Magnesium absorption is known to depend on the exact salt and preparation used, the dosage, the status of magnesium stores in the body, and hormonal factors. In general, magnesium salts that are soluble in water (e.g., magnesium chloride, magnesium citrate) are more bioavailable than water-insoluble magnesium salts. Certain magnesium preparations (e.g., magnesium sulfate and magnesium hydroxide) are known to have very poor absorption, a property used to produce their cathartic and purgative effects (e.g., diarrhea).

TABLE 2

Conventional Magnesium Salts

| Magnesium Salt | Magnesium, % by weight | Bioavailability (as fractional absorption of administered dose) |
| --- | --- | --- |
| Magnesium oxide | 60 | 4% |
| Magnesium carbonate | 45 | — |
| Magnesium hydroxide | 42 | 4% |
| Magnesium citrate | 15 | 12% |
| Magnesium lactate | 12 | 12% |
| Magnesium chloride | 12 | 12% |
| Magnesium sulfate | 10 | 4% |

Data obtained from http://ods.od.nih.gov/factsheets/magnesium.asp on 6 Jun. 2008.
Bioavailability data taken from M. Firoz and M. Graber, Bioavailability of US commercial magnesium preparations. Magnesium Research 14: 257-262, 2001, and references therein.

As was true of calcium salts, magnesium salts are selected for use in conventional oral nutritional supplements on the basis of factors such as cost, availability, purity, absorbability, and an individual's tolerance to adverse taste, texture, and side effects of ingestion. Magnesium oxide is the most widely used magnesium salt in conventional supplements.

Ford and Mokdad have shown that adults who take dietary supplements ingest significantly more magnesium than those who do not. [Ford E S, Mokdad A H. Dietary magnesium intake in a national sample of U.S. adults. J Nutr 2003; 133: 2879-2882.] The study by Stendig-Lindberg et al. exemplifies the beneficial effects that may be anticipated when magnesium supplementation is used for the prevention and treatment of osteoporosis. [Stendig-Lindberg G, Tepper R, Leichter I. Trabecular bone density in a two-year controlled trial of peroral magnesium in osteoporosis. Magnesium Res 1993; 6: 155-163.] In a 2-year controlled therapeutic trial of postmenopausal women with documented osteoporosis, Stendig-Lindberg et al., reported that magnesium supplements prevented fractures and resulted in a significant increase in bone density. Daily doses started at 250 mg magnesium (610 mg magnesium hydroxide) and increased or decreased depending on individual tolerance levels to a maximum of 750 mg magnesium (1,810 mg magnesium hydroxide) daily in addition to dietary magnesium uptake estimated to be between 200 and 300 mg per day. Although there were no reported side effects of treatment and despite the apparent long-term benefit of supplementation in reducing fractures and increasing bone density, only 32% of the subjects completed the 2-year trial. Magnesium hydroxide is a white, chalky solid that absorbs moisture from saliva. Likely the distasteful, chalky taste coupled with the "pickled" sensation in the mouth and diarrhea contributed to poor compliance with the dosage regimen.

The "Achilles heel" of conventional nutritional supplements and therapies for the maintenance of bone health, optimizing bone growth, density, and microarchitecture, preventing bone fractures, and the prevention and treatment of osteoporosis is a lack of compliance with the dosage regimen. Most conventional formulations are combinations of inexpensive calcium salts and vitamin D. Despite the benefits which are known to derive from daily ingestion of one of these conventional formulations, 50% or more of the subjects fail to comply with this dosage regimen because they dislike its chalky or acid taste and the flatulence, acid regurgitation, nausea, and constipation that ensue. Further, conventional nutritional supplement formulations frequently fail to incorporate quantities of calcium, magnesium, and vitamin D sufficient to maintain bone health, and limit or preclude therapeutic response to optimize bone growth or prevent or treat osteoporosis. The present invention provides a solution to the long-felt need for useful and palatable compositions useful for bone growth, normal bone remodeling and skeletal health.

SUMMARY OF THE INVENTION

The present invention is an oral nutritional and therapeutic composition useful for building bone mass, quality, and density during growth, maintaining bone mass, quality, and density over time, reducing bone fracture risk, and treating osteoporosis, comprising a unit dosage or serving mixture of calcium succinate, magnesium R-(+)-alpha-lipoate, and vitamin D. A method of building bone mass, quality, and density during growth, maintaining bone mass, quality, and density over time, reducing bone fracture risk, and treating osteoporosis in a human, comprising administering to said human a safe and effective amount of a supplement comprising a synergistically effective amount of calcium succinate, magnesium R-(+)-alpha-lipoate, and vitamin D is also disclosed. Further, a method of preventing and treating osteoporosis in a warm-blooded animal with a therapeutically effective amount of a pharmaceutical composition comprising calcium succinate, magnesium R-(+)-alpha-lipoate, and vitamin D is disclosed. A method of preparing magnesium R-(+)-alpha-lipoate is also provided.

DETAILED DESCRIPTION OF THE INVENTION

In making this invention, the inventor has recognized that adequate daily intakes of calcium, magnesium, vitamin D, and phosphate are required for the maintenance of bone health. Phosphate is abundant in the American diet, and the average daily phosphorus intake of North American adults is about 1000 mg in women and 1500 mg in men. Between 60% and 70% of ingested phosphorus is absorbed in the jejunum and duodenum. Both intakes and absorption of phosphate are adequate for the maintenance of bone health. However, modern diets in America and other developed countries are known to be lacking in adequate calcium and magnesium for optimal bone health, as well as the vitamin D that enhances uptake of these vital minerals and provides other benefits.

The present invention is an oral nutritional and therapeutic composition useful for building bone mass, quality, and density during growth, maintaining bone mass, quality, and density over time, reducing bone fracture risk, and treating osteoporosis, comprising a unit dosage or serving mixture of calcium succinate, magnesium R-(+)-alpha-lipoate, and vitamin D. The composition is useful in men and women.

The present invention also relates to a method of building bone mass, quality, and density during growth, maintaining bone mass, quality, and density over time, reducing bone fracture risk, and treating osteoporosis in a human, comprising administering to said human a safe and effective amount of a supplement comprising a synergistically effective amount of calcium succinate, magnesium R-(+)-alpha-lipoate, and Vitamin D.

The present invention also relates to a method of supplementing vitamins and minerals required for optimization of bone growth and the maintenance of bone health in a warm-blooded animal comprising a unit dosage or serving mixture of calcium succinate, magnesium R-(+)-alpha-lipoate, and vitamin D. The method of the present invention is based on the demonstration that independently, supplemental calcium salts, magnesium salts, and vitamin D have been shown to augment bone health.

In addition, the present invention relates to a method of preventing and treating osteoporosis in a warm-blooded animal with a therapeutically effective amount of a pharmaceutical composition comprising calcium succinate, magnesium R-(+)-alpha-lipoate, and vitamin D. Included within the scope of this invention is a method of preventing and treating osteoporosis in a warm-blooded animal using oral pharmaceutical compositions comprising calcium succinate, magnesium R-(+)-alpha-lipoate, vitamin D, and a suitable pharmaceutical carrier.

Magnesium R-(+)-alpha-lipoate is not commercially available. A method of preparing magnesium R-(+)-alpha-lipoate having high purity and high chiral purity is also provided.

Calcium succinate (Chemical Abstracts Service Registry No. 140-99-8) is a white amorphous powder containing approximately 25% calcium by weight. Calcium succinate has the molecular formula $CaC_4H_4O_4$ and a molecular weight of 156.15. Calcium succinate, which is also named butanedioic acid calcium salt or succinic acid calcium salt, is available commercially (e.g., Jost Chemical Co., St. Louis, Mo.) as a salt of pharmaceutical quality, having only trace levels of toxic metal contaminants. Calcium succinate may be provided as a hydrate, a succinate salt containing both calcium and a second alkali metal ion ($Na^{1+}$, $K^{1+}$, or $Li^{1+}$) or alkaline earth metal ion ($Mg^{2+}$), a crystalline form, a polymorphic form, a form having a specific bulk density or tap density, or a form having specific particle sizes. Further, calcium succinate may be coated with pharmaceutically acceptable materials intended to modify the release and/or bioavailability of the calcium succinate (e.g., Eudragit, microcrystalline cellulose, hydroxypropylmethylcellulose phthalate, and so forth).

Magnesium R-(+)-alpha-lipoate is the magnesium salt of R-(+)-alpha-lipoic acid. Magnesium R-(+)-alpha-lipoate is a stable, non-hygroscopic, light yellow powder having a molecular formula of $Mg(C_8H_{13}O_2S_2)_2$, the general formula

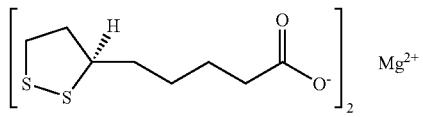

and a molecular weight of 434.94.

Magnesium R-(+)-α-lipoate has been selected because this stable salt provides both magnesium and R-(+)-alpha-lipoate, the anion of R-(+)-alpha-lipoic acid. R-(+)-α-Lipoate is the form of alpha-lipoic acid naturally found in the human body.

Alpha-Lipoic acid is a chiral compound and is available commercially as the racemic mixture, RS-alpha-lipoic acid, and as the single enantiomer, R-(+)-alpha-lipoic acid, the form of alpha-lipoic acid found in the body. RS-Alpha-lipoic acid is more stable than R-(+)-alpha-lipoic acid. RS-Alpha-lipoic acid may be stored in a closed and sealed amber container at room temperature for a year or more. In contrast, R-(+)-alpha-lipoic acid must be stored in a closed and sealed amber container at refrigerated temperatures and must be used within a few months, since it gradually polymerizes to intractable polymers and degrades by loss of sulfur-containing compounds.

Magnesium R-(+)-alpha-lipoate is not commercially available. In order to obtain sufficient quantities of this salt for use in this invention, a method of preparing magnesium R-(+)-alpha-lipoate was required. A method of preparing magnesium alpha-lipoate was disclosed by Pearson and Richardson in U.S. Pat. No. 6,288,106 B1. By this method, a solution of alpha-lipoic acid in anhydrous ethanol was added with stirring to a solution of magnesium ethoxide in anhydrous ethanol. After stirring the reaction mixture for 30 minutes, the solvent was evaporated under reduced pressure to afford the magnesium salt of alpha-lipoic acid.

Attempts to prepare magnesium R-(+)-alpha-lipoate by the method of Pearson and Richardson failed. After evaporation of the solvents, as required by the method of Pearson and Richardson, a stringy, intractable polymer was obtained; no magnesium R-(+)-alpha-lipoate was isolated.

After lengthy experimentation, the inventors have discovered that the dropwise addition of a solution of magnesium methoxide in methanol to a clear solution of R-(+)-alpha-lipoic acid in methanol-isopropyl alcohol solution maintained under an inert gas and shielded from light provides magnesium R-(+)-alpha-lipoate as a solid, pale yellow precipitate. Magnesium R-(+)-α-lipoate is isolated by filtration and purified from contaminants by washing with fresh isopropyl alcohol. Magnesium R-(+)-α-lipoate does not melt at temperatures below 300° C. Analysis for magnesium content by titration showed that the magnesium content was about 5.6% by weight, as expected. Analysis for R-(+)-α-lipoate content by HPLC showed that the R-(+)-α-lipoate was about 95% by weight, as expected. HPLC analysis also confirmed that the chiral purity was greater than 95%, confirming that no racemization occurred during reaction. Analysis of trace metals by inductively coupled plasma mass spectrometry showed that magnesium R-(+)-α-lipoate contained only very low parts per million levels of toxic metals, such as aluminum, tin, arsenic, barium, lead, and thallium. Thus, this newly discovered method of preparing magnesium R-(+)-α-lipoate uses inexpensive, commercially available reagents, reaction conditions that are easily scaled to commercial quantities, and provides greater than 65% yields of magnesium R-(+)-α-lipoate of greater than 95% purity and greater than 95% chiral purity.

Magnesium R-(+)-alpha-lipoate is insoluble in water, a property that conventionally indicates that this salt has poor bioavailability. However, the inventors have found that both magnesium and R-(+)-α-lipoate ions are available from suspensions of the salt in aqueous solutions having a pH in the range from about 4 to about 8. R-(+)-α-Lipoate has both hydrophilic and lipophilic properties. Based on this combination properties, it is chemically reasonable to expect that R-(+)-α-lipoate binds to lipophilic membranes, as are found on cells throughout the body, and is taken up, at least in part, by absorption of magnesium-bound lipoate from the gastrointestinal tract. Thus, its bioavailability is unexpectedly high, as compared to conventional, water-insoluble magnesium salts. Further, R-(+)-alpha-lipoic acid is a widely distributed physiological antioxidant that combines free radical scavenging properties with an ability, after intracellular reduction to dihydrolipoic acid, to regenerate the levels of other nonenzymatic and enzymatic antioxidants, including glutathione (GSH), ascorbate, α-tocopherol, catalase and GSH peroxidase. The physiological form of R-(+)-α-lipoate, the R-(+)-enantiomer, is present in all eukaryotic and prokaryotic cells. R-(+)-α-Lipoate has demonstrated safety and an absence of toxicity when administered chronically to humans.

The term "vitamin D" or "vitamin D material" includes vitamin D, cholecalciferol ($D_3$), ergocalciferol ($D_2$), and its biologically active metabolites and precursors, such as $1α,25$-$(OH)_2$ vitamin D; 25-(OH) vitamin D; its biological precursor; and $1α$-(OH) vitamin D and analogues of the dihydroxy compound. Calcium and magnesium absorption efficiency is probably best explained by a combination of calcitriol and 25(OH)D effects, and absorptive regulation is optimal when serum 25(OH)D concentration is relatively high. Therefore, the term also includes combinations of biologically active forms of vitamin D, cholecalciferol, ergocalciferol, and biologically active metabolites and precursors. Biologically active vitamin D metabolites and precursors possess more biopotency for bone health than vitamin $D_2$ or $D_3$. Thus, the amount of more biopotent vitamin D metabolites and precursors required to be safe, effective, and nourishing is less and will be adjusted to provide the biological and physiological effects on bone health equivalent to vitamins $D_2$ and $D_3$. Vitamin D status is currently indicated by 25-hydroxycholecalciferol ($25OHD_3$) concentration in serum.

The term "bone health" is intended to encompass enhancement of bone growth, density, and microarchitecture, and the prevention and treatment of osteoporosis Maintenance of bone health also includes reducing the risk of bone fractures, including those resulting from inadequate intakes of dietary calcium, magnesium, and vitamin D; exercise and stress; aging; medications such as steroids, certain cancer treatments, anticonvulsants, and aluminum-containing antacids; diseases of the kidney, liver, stomach, and intestines; and osteoporosis.

The term "bioavailability" refers to the amount of a substance that is absorbed in the intestines and ultimately available for biological activity in a subject's cells and tissues.

The term "excipient material" is intended to mean any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms or conditions.

The phrase "therapeutically effective" is intended to qualify the amounts of calcium succinate, magnesium R-(+)-alpha-lipoate, and vitamin D for use in the orally administered composition of this invention which will achieve the goal of providing the quantities of calcium, magnesium, and vitamin D that are needed to enhance bone growth, density, and microarchitecture, prevent bone fractures, and prevent and treat osteoporosis.

For the purpose of this disclosure, a warm-blooded animal is a member of the animal kingdom which includes but is not limited to mammals and birds. The most preferred mammal of this invention is human.

Surprisingly, the inventors have discovered that a composition comprising calcium succinate, magnesium R-(+)-alpha-lipoate, and vitamin D is a pluripotent combination of vitamins and minerals that synergistically provides key vitamins, minerals, and anti-oxidants needed for bone health. The effectiveness of the combination derives from the unexpected manner in which the three components interact to facilitate and enable the physiological activities of each other, not merely on the additive effects of the individual components. For example, vitamin D facilitates uptake of both calcium and magnesium from the gastrointestinal tract and exerts additional physiological actions not related to calcium or magnesium. Calcium modulates uptake of magnesium from the gastrointestinal tract, and magnesium modulates uptake of calcium from the gastrointestinal tract. Magnesium modulates calcium incorporation into bone and beneficially alters bone microarchitecture.

A composition of this invention is provided in a serving or dose comprising the quantities of each component listed in Table 3.

TABLE 3

Composition of each dose or serving

| | Composition of each dose or serving |
|---|---|
| Calcium succinate | 100-1000 mg (Provides 25-250 mg calcium) |
| Magnesium R-(+)-alpha-lipoate | 100-2000 mg (Provides 5-100 mg magnesium) |
| Vitamin D | 5-50 micrograms (mcg) (200-2000 IU) |

The inventors have considered the following factors in determining the quantity of calcium present in a composition of this invention. Contemporary sedentary North American and European individuals have calcium intakes of approximately 15 mmol/day. [R P Heaney and C M Weaver. Calcium and vitamin D. Endocrinol Metab Clin N Am 32, 181-194 (2003)] Since only 10% of dietary calcium is absorbed from the gut and half of that is rapidly excreted, daily net calcium absorption from a diet which provides about 15 mmol calcium is 0.75 mmol calcium. Concurrently, the body loses calcium through skin, nails, hair, sweat, and excretion. Under sedentary conditions, cutaneous losses alone are estimated to be on the order of 0.4 to 1.4 mmol calcium per day, but with exercise and sweating, such losses can rise to above 7 mmol calcium per day. (This drain is great enough to produce a measurable change in bone mass across an athletic playing season.) Hence, an intake of 15 mmol calcium per day is insufficient for skeletal maintenance in a sedentary adult, and fails to provide sufficient calcium for support of bone growth or anti-osteoporosis therapy.

The recommended dietary reference intake for pre-menopausal and perimenopausal women (age 31-50 years) and women on hormone therapy is 1,000 mg calcium/day in a combination of dietary and supplemental forms. For men and women aged 51 to 70 years, 1,200 mg calcium/day is recommended. Women older than 65 years should ingest 1,500 mg calcium/day. Modern diets frequently do not provide sufficient calcium to meet these requirements. Although it is known that calcium deficiencies can be corrected by administration of calcium supplements, conventional calcium-containing supplements have organoleptic characteristics that significantly reduce long-term compliance with daily dosage regimens. Therefore, calcium succinate, odorless and tasteless calcium salt containing 25% calcium by weight, has been selected as the calcium source in compositions of the present invention. A composition of the invention contains from 25 mg to about 250 mg calcium as calcium succinate. Oral dosage forms containing a composition of the invention comprising 25 or 50 mg calcium, on an elemental basis, in the form of calcium succinate are selected for administration to individuals who must restrict calcium intake or those who are undergoing treatment with medications generally known as bisphosphonates, for example. The highest doses of calcium (200 or 250 mg calcium) are intended to augment calcium in subjects suffering from osteoporosis. A clinician has the training and expertise to determine which dose is most appropriate for a patient.

The inventors have considered the following facts in determining the quantities of magnesium R-(+)-alpha-lipoate effects on biological systems (e.g., diarrhea) that significantly reduce long-term compliance with daily dosage regimens. Therefore, magnesium R-(+)-alpha-lipoate, an odorless and tasteless magnesium salt that provides both magnesium and the anti-oxidant R-(+)-alpha-lipoate, has been selected as the magnesium source in compositions of the present invention. A composition of the invention contains from 5 mg to about 100 mg magnesium, on an elemental basis, in the form of magnesium R-(+)-alpha-lipoate. A clinician has the training and expertise to determine which dose is most appropriate for a patient.

The vitamin D requirement, defined as the quantity the body must make or ingest each day to optimize D-related functions, is uncertain. Therefore, the inventors have considered the following factors in determining the quantity of vitamin D present in a composition of her invention. Traditional oral intake recommendations as set forth by the Food and Nutrition Board of the Institute of Medicine in 1997 (Table 5) were pegged to the amount of vitamin D required to prevent the clinical observation of rickets, but such recommendations ignore cutaneous inputs and the need to ensure extra-skeletal functions of the vitamin.

TABLE 5

Recommended Levels of Vitamin D

| | Adequate Intake Levels | | Tolerable Upper Intake Levels | | | | |
|---|---|---|---|---|---|---|---|
| Age | Children | Men & Women | Children | Men | Women | Pregnancy | Lactation |
| Birth to 1 year | 5 mcg (200 IU) | | 25 mcg (1,000 IU) | | | | |
| 1-14 years | | | 50 mcg (2,000 IU) | | | | |
| 14-18 years | | 5 mcg (200 IU) | | 50 mcg (2,000 IU) | 50 mcg (2,000 IU) | 50 mcg (2,000 IU) | 50 mcg (2,000 IU) |
| 19-50 years | | 5 mcg (200 IU) | | 50 mcg (2,000 IU) | 50 mcg (2,000 IU) | 50 mcg (2,000 IU) | 50 mcg (2,000 IU) |
| 51-70 years | | 10 mcg (400 IU) | | 50 mcg (2,000 IU) | 50 mcg (2,000 IU) | 50 mcg (2,000 IU) | 50 mcg (2,000 IU) |
| 71+ years | | 15 mcg (600 IU) | | 50 mcg (2,000 IU) | 50 mcg (2,000 IU) | 50 mcg (2,000 IU) | 50 mcg (2,000 IU) |

[Data obtained from http://ods.od.nih.gov/factsheets/VitaminD_pf.asp on Jul. 2, 2008.]

included in a composition of this invention. The recommended dietary allowance for magnesium for children and adults is shown in Table 4.

TABLE 4

Recommended Dietary Allowances for Magnesium

| Age (Years) | Male (mg/day) | Female (mg/day) | Pregnancy (mg/day) | Lactation (mg/day) |
|---|---|---|---|---|
| 1-3 | 80 | 80 | | |
| 4-8 | 130 | 130 | | |
| 9-13 | 240 | 240 | | |
| 14-18 | 410 | 360 | 400 | 360 |
| 19-30 | 400 | 310 | 350 | 310 |
| 31+ | 420 | 320 | 360 | 320 |

Data obtained from http://ods.od.nih.gov/factsheets/magnesium.asp on 6 Jun. 2008.

Modern diets frequently do not provide sufficient magnesium to meet these requirements. Although it is known that magnesium deficiencies can be corrected by administration of magnesium supplements, conventional magnesium-containing supplements have organoleptic characteristics and Current evidence indicates that a healthy adult has daily vitamin D inputs from all sources in the range of 3000 to 5000 IU (75 to 125 micrograms). Although this may be sufficient for healthy adults with sufficient sun exposure, it may not meet the requirements in certain subjects, such as adolescents, young women, or older individuals who have both reduced sun exposure and reduced efficiency of photoconversion of 7-dehydrocholesterol to vitamin $D_3$. Therefore, the inventors have provided doses of vitamin D that are safe, effective, and nourishing. The amount of vitamin D in a composition of this invention will generally comprise from about 5 micrograms to about 50 micrograms of vitamin D material. Biologically active vitamin D metabolites and precursors possess more biopotency for bone health than vitamin $D_2$ or $D_3$. Thus, the amount of more biopotent vitamin D metabolites and precursors required to be safe, effective, and nourishing is less and will be adjusted to provide the biological and physiological effects on bone health equivalent to vitamins $D_2$ and $D_3$.

A composition of the present invention affords significant advantages over conventional calcium supplements. For example, calcium succinate is a tasteless and odorless salt with a high percentage of calcium by weight. It is a stable and safe powder that is commercially available as a pharmaceutical quality ingredient having trace levels of toxic metals. By comparison, conventional calcium citrate and calcium acetate are known to have toxic contaminants, undesirable organoleptic properties and adverse side effects when administered orally. It is known that undesirable organoleptic properties significantly reduce compliance with dosage regimens that support bone health long-term. Likewise, magnesium R-(+)-alpha-lipoate is an odorless and tasteless salt of R-(+)-alpha-lipoic acid which provides the benefits of both magnesium and R-(+)-alpha-lipoate, the natural form of alpha-lipoic acid. By comparison, conventional magnesium salts are chalky powders with repugnant organoleptic properties such as "pickle" mouth. Further, the combination of calcium and magnesium provided by a composition of the present invention affords the significant advantage that both cations are provided in quantities sufficient to support bone health. Conventional calcium supplements often lack magnesium. Further, magnesium is a natural "stool softener" and will mitigate the constipation brought about by calcium. Magnesium R-(+)-alpha-lipoate concomitantly provides R-(+)-alpha-lipoate, a widely distributed physiological antioxidant that combines free radical scavenging properties with an ability, after intracellular reduction to dihydrolipoic acid, to regenerate the levels of other nonenzymatic and enzymatic antioxidants, including glutathione (GSH), ascorbate, α-tocopherol, catalase and GSH peroxidase. Hypertension, diabetes, and heart disease are serious diseases that accompany aging, accelerate physiological dysfunction, a decline in the quality of life, and death. Administration of lipoic acid to a subject having hypertension, diabetes, or heart disease is known to reduce the cellular and tissue dysfunction that characterizes each of these disease states [Fuchs, J, Packer, L. and Zimmer, G. (Eds). *Lipoic Acid in Health and Disease*, Marcel Dekker, New York, 1997.]. Finally, sufficient vitamin D is provided in a composition of the present invention to optimize the effects of calcium and magnesium. The provision of sufficient vitamin D ensures optimal absorption and utilization for bone health and renders a composition of the present invention advantageously superior to conventional calcium supplements, which often fail to supply sufficient vitamin D.

Finally, the inventors have considered the clinical observation that many of the current calcium supplement tablets are too large, difficult to swallow, and not easily incorporated into a daily routine. [Kessenich C R. Alternative choices for calcium supplementation. J Nurse Practitioners 2008; 4(1): 36-39.] Supplements in pill form often cause nausea, indigestion, constipation, and bloating. As a result, conventional calcium supplements are often left in the medicine cabinet or the drawer, and patients fail to comply with prescribed dosing regimens.

The compositions of this invention can be administered by any means that effects contact of the active ingredients with the site of action in the body of a warm-blooded animal. A most preferred means of administration is by the oral route (i.e., ingestion). The compositions of this invention can be administered one or more times each day, so as to facilitate and enhance compliance with dosage regimens.

The active ingredients can be administered by the oral route in solid dosage forms, such as tablets, capsules, and powders, or in liquid dosage forms, such as elixirs, syrups, and suspensions. The pharmaceutical composition is preferably made in the form of a dosage unit containing a particular amount of each active ingredient. One most preferred oral dosage form of a composition of the present invention is an admixture of powders contained within a sachet. Because a composition of the present invention is not hygroscopic and has no repugnant taste or odor, the admixture of powders comprising a composition of the present invention can be sprinkled on food or stirred into beverages to enhance ease of use and support high levels of compliance with daily dosage regimens.

In general, the pharmaceutical dosage forms of compositions of this invention can be prepared by conventional techniques, as are described in *Remington's Pharmaceutical Sciences*, a standard reference in this field [Gennaro A R, Ed. *Remington: The Science and Practice of Pharmacy.* 20$^{th}$ Edition. Baltimore: Lippincott, Williams & Williams, 2000]. For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration are well and widely known in the pharmaceutical art.

Dosing for oral administration may be with a regimen calling for single daily dose, or for a single dose every other day, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to several hours, depending upon the properties of each active agent such a potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

Clinical Uses of a Composition of this Invention. In addition to uses of this invention for building bone mass, quality, and density during growth, maintaining bone mass, quality, and density over time, preventing bone fractures, and treating osteoporosis in men and women, a composition of this invention has other known uses. Teegarden and colleagues have reported that young women who were taking oral contraceptives had a dietary calcium intake of less than 800 mg calcium per day. Increasing daily calcium intake prevented a drop in bone mineral density at the hip and the spine. [Teegarden D, Legowski P, Gunther C W, McCabe G P, Peacock M, Lyle R M. Dietary calcium intake protects women consuming oral contraceptives from spine and hip bone loss. J Clin Endocrinol Metab 2005 September; 90(9): 5127-33.] McCann and Ames concluded that there is ample biological evidence to suggest an important role for vitamin D in brain development and function. They also recommended vitamin D supplementation of at-risk groups, including nursing infants, the elderly, and African-Americans. [McCann J C, Ames B N. Is there convincing biological or behavioral evidence linking vitamin D deficiency to brain dysfunction? FASEB J 2008; 22: 1-20.] Grau, Baron, et al. reported that long term use of calcium supplements provides a protective effect against development of potentially precancerous colon polyps that lasts for years. It is the only dietary substance that has been shown to be chemoprotective against development of colorectal polyps. [Grau M V, Baron J A, Sandier R S, Wallace K, Haile R W, Church T R, Beck G J, Summers R W, Barry E L, Cole B F, Snover D C, Rothstein R, Mandel J S. Prolonged effect of calcium supplementation on risk of colorectal adenomas in a randomized trial. J Natl Cancer Inst 2007 Jan. 17; 99(2): 129-36.] Likewise, large doses of vitamin D, ingested as calcium and vitamin D supplements, may reduce incidence of all cancers. [Lappe J M, Travers-Gustafson D, Davies K M, Recker R R, Heaney R P. Vitamin D and calcium supplementation reduces cancer risk: results of a randomized trial. Am J Clin Nutr 2007 June; 85(6): 1586-91.] Further, there is growing evidence that calcitriol protects against oxidative stress in nonmalignant human prostate epithelial cells, but acts as a pro-oxidant in cancer calls. [Bao B-Y, Ting H-J, Hsu J-W, Lee Y-F. Protective role of 1a,25-dihydroxyvitamin D3 against oxidative stress in nonmalignant human prostate epithelial cells. Int J Cancer 2008; 122: 2699-2706.] Ecological and observational studies suggest that low vitamin D status could be associated with higher mortality from life-threatening conditions including cancer, cardiovascular disease, and diabetes mellitus that account for 60% to 70% of total mortality in high-income countries such as the United States. [Autier P, Gandini S. Vitamin D supplementation and total mortality. Arch Intern Med 2007, 67(16): 1730-1737.]

Example 1

Preparation and Analysis of Magnesium R-(+)-Alpha-Lipoate

A. Attempted methods of preparing magnesium R-(+)-alpha-lipoate. Seven different reactions were carried out repetitively in an attempt to prepare magnesium R-(+)-alpha-lipoate (Table 6). Each product was analyzed for magnesium content by titration with eriochrome black and for R-(+)-alpha-lipoate content by HPLC.

TABLE 6

Attempted methods of preparing magnesium R-(+)-alpha-lipoate

| Rx. | R-(+)-alpha-Lipoic Acid | Mg Reagent | Conditions | Result |
|---|---|---|---|---|
| A | R-(+)-α-lipoic acid; 2 equivalents dissolved in anhydrous ethanol | 1 equivalent of magnesium ethoxide in anhydrous ethanol | Reaction at room temperature | Evaporation of the solvent, as disclosed in U.S. Pat. No. 6,288,106, left a stringy, intractable polymeric gum that could not be dissolved in water, organic solvents, or acids. Analytical results indicated that the product was not magnesium R-(+)-alpha-lipoate. |
| B | R-(+)-α-lipoic acid; 2 equivalents dissolved in acetone | 1 equivalent of magnesium methoxide in anhydrous methanol | Reaction at room temperature | A green solid precipitated and was isolated by filtration. The solid could not be dissolved in water, organic solvents, or acids. Analytical results indicated that the product was not magnesium R-(+)-alpha-lipoate. |
| C | R-(+)-α-lipoic acid; 2 equivalents dissolved in methanol | 1 equivalent of magnesium methoxide in anhydrous methanol | Reaction at room temperature | No solid precipitated from the reaction. |
| D | R-(+)-α-lipoic acid; 2 equivalents dissolved in ethanol | 1 equivalent of magnesium methoxide in anhydrous methanol | Reaction at room temperature | No solid precipitated from the reaction |
| E | R-(+)-α-lipoic acid; 2 equivalents dissolved in acetonitrile | 1 equivalent of magnesium methoxide in anhydrous methanol | Reaction at room temperature | A mixture of green solid and yellow-green solid precipitated and was isolated by filtration. The solids did not completely dissolve in organic solvents or acids. Analytical results indicated that the product was not magnesium R-(+)-alpha-lipoate. |
| F | R-(+)-α-lipoic acid; 2 equivalents dissolved in isopropyl alcohol | 1 equivalent of magnesium t-butoxide in anhydrous ethanol/acetonitrile | Reaction at room temperature | A pale yellow solid precipitated and was isolated by filtration. The yield of product was about 50% of theoretical. Analytical results indicated that the product was magnesium R-(+)-alpha-lipoate. |

TABLE 6-continued

Attempted methods of preparing magnesium R-(+)-alpha-lipoate

| Rx. | R-(+)-alpha-Lipoic Acid | Mg Reagent | Conditions | Result |
|---|---|---|---|---|
| G | R-(+)-α-lipoic acid; 2 equivalents dissolved in acetonitrile | 1 equivalent of magnesium methoxide in anhydrous methanol | Reaction at room temperature | A pale yellow solid precipitated and was isolated by filtration. Analytical results indicated that the product was magnesium mono-R-(+)-alpha-lipoate mono-acetylacetonate. |

B. Method of preparation of magnesium R-(+)-alpha-lipoate of this invention. Dropwise addition of a solution of magnesium methoxide in methanol in a volume equivalent to about one mole of magnesium methoxide to a clear solution of about two moles of R-(+)-alpha-lipoic acid in methanol-isopropyl alcohol solution maintained under an inert gas and shielded from light provided magnesium R-(+)-alpha-lipoate as a solid, pale yellow precipitate. Magnesium R-(+)-α-lipoate was isolated by filtration and purified from contaminants by washing with fresh isopropyl alcohol. Magnesium R-(+)-α-lipoate did not melt at temperatures below 300° C. Analysis for magnesium content by titration showed that the magnesium content was 5.6% by weight, as expected. Analysis for R-(+)-α-lipoate content by HPLC showed that the R-(+)-α-lipoate was 94.4% by weight, as expected. HPLC analysis by a method useful for the determination of chiral purity confirmed that no racemization occurred during reaction. Analysis of trace metals by inductively coupled plasma mass spectrometry showed that magnesium R-(+)-α-lipoate contained only very low parts per million levels of toxic metals, such as aluminum, tin, arsenic, barium, lead, and thallium. Magnesium R-(+)-α-lipoate was obtained in greater than 65% yields and had greater than 95% purity and greater than 95% chiral purity.

The following examples present hypothetically useful therapeutic uses of representative pharmaceutical compositions of the present invention and their anticipated outcomes in building bone mass, quality, and density during growth, maintaining bone mass, quality, and density over time, reducing bone fracture risk, and treating osteoporosis in subjects requiring such treatment. The examples are representative of the scope of the invention, and as such are not to be considered or construed as limiting the invention recited in the appended claims.

Example 2

Male Sprague-Dawley rats (Harlan Inc., Indianapolis, Ind.) 3 months old, weighing 250-275 g, will be randomly divided into groups of 10 rats each. The rats will be individually housed in stainless steel cages in an environmentally controlled room (temperature, 20° C.; relative humidity, 30%-60%; reversed light:dark cycle, 12:12 hr). The rats will be fed ad libitum pelleted laboratory rat chow adequate in nutrients (Purina Mills, Inc., St Louis, Mo.) and deionized water. All animals will be moved to metabolic cages 12 hrs prior to gavaging. The animals will be fasted overnight preceding and food will be resumed 3 hrs after the gavage.

Femur uptake of $^{45}$Ca will be used to measure the fractional absorption of calcium from the magnesium lipoate/calcium succinate composition. (Labeling of magnesium lipoate with the radioactive isotope magnesium-28 is beyond the scope of this study, since this isotope is short-lived and is not commercially available.) Rats (n=10/group) will be assigned to receive magnesium lipoate/calcium succinate at a low dose of 3.6 mg calcium or a high dose of 25 mg calcium, representing one third of the daily requirement for a rat. Slurries of magnesium lipoate/calcium succinate will be prepared by labeling with radioactive calcium containing either 20 or 10 μCi $^{45}$Ca/mL from concentrated $^{45}$Ca solution (2 mCi/mL). The slurries will be delivered directly to the stomach of the animals. Each dose will contain 9 μCi $^{45}$Ca as $CaCl_2$. For each study, 10 additional rats (IP group) will receive an intraperitoneal injection of 9 μCi $^{45}$Ca as $CaCl_2$ to mimic 100% absorption. Femurs of the rats will be taken 48 hours after gavage. Fractional absorption will be determined by radioactive uptake of $^{45}$Ca into the right femur of rats according to the following equation:

$$\text{Percent absorption} = \frac{(\% \text{ dose in the femur of experimental group}) \times 100}{(\% \text{ dose in the femur of the } IP \text{ group})}$$

The ratio can be used to assess calcium absorption because transport of calcium after crossing the gut subsequent to dissociation of calcium from its ligands and subsequent uptake of $^{45}$Ca by femurs would be equal for rats on oral and intraperitoneal (IP) doses. Relative differences in bioavailability using this model parallel results of human studies.

It is anticipated that the fractional absorption of calcium from a magnesium lipoate/calcium succinate composition will be at least about 50% from the 3.6 mg calcium load and at least about 40% from the 25 mg calcium load. If such results are observed, it will confirm that the calcium from calcium succinate in the composition is bioavailable and useful for bone growth and skeletal remodeling in the rat.

Example 3

About 240 healthy, post-menopausal women age 60 years or older are treated by ingesting, thrice daily, a composition containing calcium succinate and magnesium R-(+)-alpha-lipoate in the portions described in Table 6.

TABLE 6

Test Composition

| Component | Weight |
|---|---|
| Calcium succinate | 1,000 mg (250 mg Ca) |
| Magnesium R-(+)-alpha-lipoate | 1,790 mg (100 mg Mg) |

The dosage is provided as a swallowable tablet dosage form or as a mixture of dry powders contained in a paper sachet. The tablet formulation is made by milling each formulation component to a fine powder, thoroughly admixing the powders, adding release agents, and tabletting using a standard tablet press, to form tablets weighing approximately 2,720 milligrams. The tablets are then coated, using a pan coater. The coating solution contains approximately 11% hydroxypropylmethyl cellulose, approximately 2% polyethylene glycol, approximately 3.5% colorant, and the balance of water. The sachet formulation is made by milling each formulation component to a fine powder, thoroughly admixing the powders, and apportioning the admixture into paper sachets such that each sachet contains 1,000 mg calcium succinate and 1,790 mg magnesium R-(+)-alpha-lipoate.

One half of the women receive a supplement containing 400 IU of vitamin D while the other half of the women receives a placebo. Both the vitamin D supplement and placebo contain 127 mg of calcium as calcium phosphate. All the women receive the test composition, and have the option of selecting to ingest the tablet or powder dosage form according to their personal preference.

At the beginning of the study and after one year, the bone density of the spine and overall body bone density are measured by dual x-ray absorptiometry. It is anticipated that the measurements will demonstrate a change in the bone density of the spine that is statistically significant and shows a net increase in bone density. It is expected that the change in whole body bone density will or will not be significantly different. If it is observed that the change in whole body density is not significantly different, it will mean there was no gain in the whole body bone density, and it also will mean that the women did not lose bone density over the year, a loss which is expected in normal post-menopausal women not taking calcium supplements. Further, it is anticipated that the test composition/placebo patients will not lose bone in the spine or whole body, but they may not gain bone as will those taking supplemental vitamin D.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present invention to its fullest extent. The specific embodiments are, therefore, to be construed as merely illustrative, and not limitative of the remainder of the disclosure in any way whatsoever.

We claim:

1. A method of building bone mass, strength, microarchitecture, and density during growth, maintaining bone mass, strength, microarchitecture, and density over time, reducing bone fracture risk, and treating osteoporosis in a human, comprising administering to a human a safe and effective amount of a composition comprising an effective amount of calcium succinate, magnesium R-(+)-alpha-lipoate, and a vitamin D material selected from the group consisting of vitamin $D_3$, vitamin $D_2$, $25(OH)D_3$, $25(OH)D_2$, $1\alpha,25(OH)_2D_3$, $1\alpha,25(OH)_2D_2$, and mixtures thereof wherein said safe and effective amount of said supplement is sufficient to achieve an effect selected from the group consisting of building bone mass, strength, microarchitecture, and density during growth, maintaining bone mass, strength, microarchitecture, and density over time, reducing bone fracture risk, and treating osteoporosis in a human, wherein said magnesium R-(+)-alpha-lipoate has greater than 95% purity and greater than 95% chiral purity.

2. The method of claim 1, wherein said calcium succinate is administered at a level to provide from about 25 milligrams to about 1,000 milligrams of calcium, on an elemental basis, per day; said magnesium R-(+)-alpha-lipoate is administered at a level to provide from about 5 milligrams to about 400 milligrams magnesium, on an elemental basis, and from about 400 mg to about 16,000 mg R-(+)-alpha-lipoate per day; and said vitamin D material is administered at a level equivalent to from about 5 to about 50 micrograms of vitamin $D_3$, wherein said magnesium R-(+)-alpha-lipoate has greater than 95% purity and greater than 95% chiral purity.

3. The method of claim 1 wherein said composition is administered for a period of time sufficient to increase the absolute skeletal mass of said human by at least about 0.1%.

4. The method of claim 1, wherein said human has osteoporosis.

5. A method comprising administering to a human a safe and effective amount of a supplement comprising a unit dosage or serving mixture of:
   a) from about 25 milligrams to about 250 milligrams of calcium, on an elemental basis, in the form of calcium succinate;
   b) from about 5 milligrams to about 100 milligrams magnesium, on an elemental basis, and from about 400 milligrams to about 4,000 milligrams R-(+)-alpha-lipoate in the form of magnesium R-(+)-alpha-lipoate, wherein said magnesium R-(+)-alpha-lipoate has greater than 95% purity and greater than 95% chiral purity; and
   c) an amount of vitamin D material, selected from the group consisting of vitamin $D_3$, vitamin $D_2$, $25(OH)D_3$, $25(OH)D_2$, $1\alpha,25(OH)_2D_3$, $1\alpha,25(OH)_2D_2$, and mixtures thereof, equivalent to from about 5 to about 50 micrograms of vitamin $D_3$.

6. The method of claim 5, wherein said human has osteoporosis.

* * * * *